United States Patent
Libbus

(10) Patent No.: US 8,965,503 B2
(45) Date of Patent: Feb. 24, 2015

(54) SYSTEMS AND METHODS FOR TREATING SUPRAVENTRICULAR ARRHYTHMIAS

(75) Inventor: Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 57 days.

(21) Appl. No.: 13/555,784

(22) Filed: Jul. 23, 2012

(65) Prior Publication Data

US 2012/0290026 A1   Nov. 15, 2012

Related U.S. Application Data

(62) Division of application No. 11/677,116, filed on Feb. 21, 2007, now Pat. No. 8,233,982.

(51) Int. Cl.
| | | |
|---|---|---|
| *A61N 1/00* | (2006.01) | |
| *A61N 1/36* | (2006.01) | |
| *A61N 1/362* | (2006.01) | |
| *A61N 1/39* | (2006.01) | |

(52) U.S. Cl.
CPC .......... *A61N 1/36114* (2013.01); *A61N 1/3621* (2013.01); *A61N 1/3962* (2013.01)
USPC ........................................................ 607/14

(58) Field of Classification Search
CPC  A61N 1/36114; A61N 1/3621; A61N 1/3952
USPC ...................... 607/6, 7, 14, 118; 600/515–518
See application file for complete search history.

(56) References Cited

U.S. PATENT DOCUMENTS

| | | |
|---|---|---|
| 4,428,378 A | 1/1984 | Anderson et al. |
| 4,726,380 A | 2/1988 | Vollmann et al. |
| 4,830,006 A | 5/1989 | Haluska et al. |
| 4,880,005 A | 11/1989 | Pless et al. |
| 4,903,701 A | 2/1990 | Moore et al. |
| 5,154,172 A | 10/1992 | Terry, et al. |
| 5,199,248 A | 4/1993 | Hale |
| 5,199,428 A | 4/1993 | Obel et al. |
| 5,203,326 A | 4/1993 | Collins |

(Continued)

FOREIGN PATENT DOCUMENTS

| | | |
|---|---|---|
| EP | 0688577 A1 | 12/1995 |
| JP | 2004533297 A | 11/2004 |

(Continued)

OTHER PUBLICATIONS

"U.S. Appl. No. 11/677,116, Response filed Oct. 13, 2011 to Final Office Action mailed Apr. 15, 2011", 13 pgs.

(Continued)

*Primary Examiner* — Mark W Bockelman
(74) *Attorney, Agent, or Firm* — Schwegman Lundberg & Woessner, P.A.

(57) ABSTRACT

In various method embodiments, a supraventricular arrhythmia event is detected, and a supraventricular arrhythmia treatment, including neural stimulation to elicit a sympathetic response, is delivered in response to a detected supraventricular arrhythmia event. Some embodiments detect a precursor for a supraventricular arrhythmia episode, and deliver prophylactic neural stimulation to avoid the supraventricular arrhythmia event. Some embodiments detect a supraventricular arrhythmia episode, and deliver therapeutic neural stimulation for the supraventricular arrhythmia event.

20 Claims, 9 Drawing Sheets

(56) References Cited

U.S. PATENT DOCUMENTS

| | | | |
|---|---|---|---|
| 5,330,505 | A | 7/1994 | Cohen |
| 5,356,425 | A | 10/1994 | Bardy et al. |
| 5,464,434 | A | 11/1995 | Alt |
| 5,522,854 | A | 6/1996 | Ideker et al. |
| 5,564,434 | A | 10/1996 | Halperin et al. |
| 5,700,282 | A | 12/1997 | Zabara |
| 5,755,736 | A | 5/1998 | Gillberg et al. |
| 6,134,470 | A | 10/2000 | Hartlaub |
| 6,292,695 | B1 | 9/2001 | Webster, Jr. et al. |
| 6,511,500 | B1 | 1/2003 | Rahme |
| 6,564,096 | B2 | 5/2003 | Mest |
| 6,690,971 | B2 | 2/2004 | Schauerte et al. |
| 6,719,701 | B2 | 4/2004 | Lade |
| 6,937,896 | B1 | 8/2005 | Kroll |
| 7,020,530 | B1 | 3/2006 | Ideker et al. |
| 7,149,574 | B2 | 12/2006 | Yun et al. |
| 8,233,982 | B2 | 7/2012 | Libbus |
| 2002/0120304 | A1 | 8/2002 | Mest |
| 2002/0165586 | A1 | 11/2002 | Hill et al. |
| 2004/0199210 | A1 | 10/2004 | Shelchuk |
| 2004/0254612 | A1 | 12/2004 | Ezra et al. |
| 2006/0253157 | A1 | 11/2006 | Libbus et al. |
| 2007/0260283 | A1 | 11/2007 | Li |
| 2008/0086174 | A1 | 4/2008 | Libbus et al. |
| 2008/0086175 | A1 | 4/2008 | Libbus et al. |
| 2008/0200960 | A1 | 8/2008 | Libbus |
| 2009/0198294 | A1 | 8/2009 | Rossing et al. |

FOREIGN PATENT DOCUMENTS

| | | |
|---|---|---|
| WO | WO-2006127248 A1 | 11/2006 |
| WO | WO-2008103233 A1 | 8/2008 |

OTHER PUBLICATIONS

"U.S. Appl. No. 11/677,116, Final Office Action mailed Apr. 15, 2011", 17 pgs.

"U.S. Appl. No. 11/677,116, Final Office Action mailed Nov. 16, 2010", 11 pgs.

"U.S. Appl. No. 11/677,116, Non-Final Office Action mailed Jun. 26, 2009", 5 pgs.

"U.S. Appl. No. 11/677,116, Notice of Allowance mailed Apr. 3, 2012", 5 pgs.

"U.S. Appl. No. 11/677,116, Response filed Jan. 18, 2011 to Final Office Action mailed Nov. 16, 2010", 14 pgs.

"U.S. Appl. No. 11/677,116, Response filed Feb. 8, 2010 to Restriction Requirement mailed Jan. 4, 2010", 8 pgs.

"U.S. Appl. No. 11/677,116, Response filed Sep. 28, 2009 to Non Final Office Action mailed Jun. 26, 2009", 11 pgs.

"U.S. Appl. No. 11/677,116, Restriction Requirement mailed Jan. 11, 2010", 7 pgs.

"U.S. Appl. No. 12/422,147, Preliminary Statement filed Apr. 10, 2009", 2 pgs.

"European Application Serial No. 08725096.5, Office Action mailed May 16, 2012", 4 pgs.

"European Application Serial No. 08725096.5, Response filed Apr. 13, 2012 to Office Action mailed Oct. 28, 2011", 15 pgs.

"European Application Serial No. 08725096.5, Communication mailed Sep. 30, 2009", 2 pgs.

"European Application Serial No. 08725096.5, Office Action mailed Jan. 19, 2010", 3 pgs.

"European Application Serial No. 08725096.5, Office Action mailed Oct. 28, 2011", 4 pgs.

"European Application Serial No. 08725096.5, Response filed Oct. 20, 2009 to Communication mailed Sep. 30, 2009", 9 pgs.

"European Application Serial No. 08725096.5, Response filed Apr. 15, 2010 to Office Action mailed Jan. 19, 2010", 15 pgs.

"International Application Serial No. PCT/US2008/001407, Written Opinion mailed Jul. 15, 2008", 7 pgs.

"International Application Serial No. PCT/US2008/001407, Search Report mailed Jul. 15, 2008", 4 pgs.

"Japanese Application Serial No. 2009-550875, Office Action mailed Nov. 22, 2011", (w/ English Translation), 7 pgs.

"Japanese Application Serial No. 2009-550875, Response filed Feb. 22, 2012 to Office Action mailed Nov. 22, 2011", (w/ English Transation of Amended Claims), 8 pgs.

Ali, I. M, "Modification of supraventricular tachyarrhythmias by stimulating atrial neurons", Ann Thorac Surg, 50(2), (Aug. 1990), 251-6.

Cardinal, R., et al., "Spinal cord stimulation suppresses bradycardias and atrial tachyarrhythmias induced by mediastinal nerve stimulation in dogs", Am J Physiol Regul Integr Comp Physiol, 291, (2006), R1369-R1375.

Hageman, G. R., et al., "Direct and reflex cardiac bradydysrhythrnias from small vagal nerve stimulations", Am Heart J., 89(3), (1975), 338-48.

Hageman, G. R., et al. "Neurally induced cardiac arrhythmias", The Physiologist, 15, (1972), 157.

Randall, W. C., et al., "Autonomic neural control of cardiac rhythm: the role of autonomic imbalance in the genesis of cardiac dysrhythmia.", Cardiology, 61(1), (1976), 20-36.

Takahashi, Takeo, "Atlas of the Human Body", Harper Collins, (1989), 132-133.

Thompson, Gregory W, "Bradycardia induced by intravascular versus direct stimulation of the vagus nerve", Annals of Thoracic Surgery, 65(3), (Mar. 1998), 637-642.

Verrier, R., et al., "Autonomic aspects of arrhythmogenesis: the enduring and the new.", Curr Opin Cardiol., 19(1), (2004), 2-11.

"European Application Serial No. 08725096.5, Response filed Sep. 7, 2012 to Examination Notification Art. 94(3) mailed May 16, 2012", 7 pages.

"European Application Serial No. 08725096.5, Summons to attend oral proceedings dated Dec. 13, 2012", 6.

SYSTEMS AND METHODS FOR TREATING SUPRAVENTRICULAR ARRHYTHMIAS

CLAIM OF PRIORITY

This application is a division of and claims the benefit of priority under 35 U.S.C. §120 to U.S. patent application Ser. No. 11/677,116, filed on Feb. 21, 2007, now issued as U.S. Pat. No. 8,233,982, which is hereby incorporated by reference herein in its entirety.

FIELD

This application relates generally to medical devices and, more particularly, to systems, devices and methods for treating supraventricular arrhythmias,

BACKGROUND

The heart is the center of a person's circulatory system. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. Contractions of the myocardium provide these pumping functions. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system cause the various portions of the heart to contract in synchrony, which efficiently pumps the blood. Blocked or abnormal electrical conduction or deteriorated myocardial tissue causes dysynchronous contraction of the heart, resulting in poor hemodynamic performance, including a diminished blood supply to the heart and the rest of the body. Heart failure occurs when the heart fails to pump enough blood to meet the body's metabolic needs.

Tachyarrhythmias are abnormal heart rhythms characterized by a rapid heart rate. Examples of tachyarrhythmias include supraventricular arrhythmias or supraventricular tachycardias (SVTs), and the more dangerous ventricular tachyarrhythmias which include ventricular tachycardia (VT) and ventricular fibrillation (VF). A supraventricular tachyarrhythmia (SVT) is an arrhythmia that originates from the supraventricular region, such as the atrium, the sinus node, the AV node or AV junction. Examples of SVT include atrial tachyarrhythmia (AT) as well as AV and AV Nodal Reentry Tachyarrhythmias (AVNRT). Atrial tachyarrhythmia includes atrial tachycardias such as atrial flutter, and further includes atrial fibrillation, for example. SVT can be conducted through the AV node, thus resulting in a ventricular tachyarrhythmia associated with the SVT, Thus, an atrial tachycardia can evolve into more serious arrhythmias like ventricular tachycardia.

Some SVTs are chronic in nature, whereas others are not chronic. The duration of these non-chronic SVTs can range from a time period of less than a minute to a time period of several days, An example of a non-chronic SVT is paroxysmal atrial tachycardia (PAT), which also may be referred to as paroxysmal SVT, AVNRT or AV reentry tachycardia. PAT is a type of rapid atrial arrhythmia characterized by brief periods of sudden-onset and often abrupt termination of atrial tachycardia. The sudden onset of the tachycardia is caused by micro-reentry within the AV node or macro-reentry between the AV node and a bypass tract, and can be associated with uncomfortable and annoying symptoms such as lightheadedness, chest pain, palpitations, anxiety, sweating and shortness of breath.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of cardiac rhythm management (CRM) devices known as an implantable cardioverter defibrillator (ICD) provides this kind of therapy by delivering a shock pulse to the heart when the device detects tachyarrhythmias. Some SVTs, such as PAT, can be difficult to treat because it typically is not considered to be lethal enough to warrant defibrillation shock treatment. Another type of electrical therapy for tachycardia is anti-tachycardia pacing (ATP). Modern ICDs typically have ATP capability, and deliver ATP therapy or a shock pulse when a tachyarrhythmia is detected.

Cardioversion/defibrillation consumes a relatively large amount of stored power from the battery and can cause patient discomfort. It is desirable, therefore, to terminate a tachyarrhythmia whenever possible without using shock therapy. Devices have therefore been programmed to use ATP to treat lower rate tachycardias and to use cardioversion/defibriliation shocks to terminate fibrillation and certain high rate tachycardias.

SUMMARY

Various device embodiments comprise a controller, a sensor, and a neural stimulator. The sensor is adapted to cooperate with the controller to detect a supraventricular arrhythmia event. The neural stimulator is adapted to stimulate a neural target to elicit a sympathetic response. The controller is adapted to control the neural stimulator to stimulate the neural target in response to the detected supraventricular arrhythmia event.

Various system embodiments comprise means for detecting a supraventricular arrhythmia event, and means for delivering a supraventricular arrhythmia treatment in response to a detected supraventricular arrhythmia event. The means for delivering a supraventricular arrhythmia treatment includes means for delivering neural stimulation to elicit a sympathetic response.

In various method embodiments, a supraventricular arrhythmia event is detected, and a supraventricular arrhythmia treatment, including neural stimulation to elicit a sympathetic response, is delivered in response to a detected supraventricular arrhythmia event. Some embodiments detect a precursor for a supraventricular arrhythmia episode, and deliver prophylactic neural stimulation in avoid the supraventricular arrhythmia event. Some embodiments detect a supraventricular arrhythmia episode, and deliver therapeutic neural stimulation for the supraventricular arrhythmia event.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to

DETAILED DESCRIPTION

Figure 1:
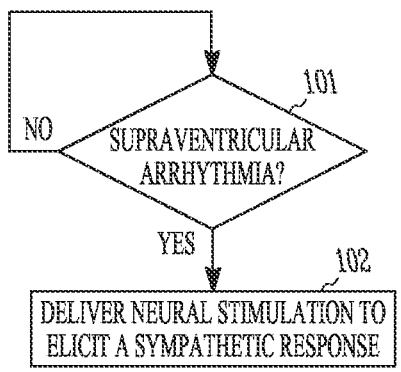
FIG. 1 illustrates an embodiment of an atrial arrhythmia therapy.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Heart rate and force is increased when the sympathetic nervous system is stimulated, and is decreased when the sympathetic nervous system is inhibited (the parasympathetic nervous system is stimulated). Cardiac rate, contractility, and excitability are known to be modulated by centrally mediated reflex pathways. Baroreceptors and chemoreceptors in the heart, great vessels, and lungs, transmit cardiac activity through parasympathetic and sympathetic afferent fibers to the central nervous system. Activation of sympathetic afferents triggers reflex sympathetic activation, vasoconstriction, and tachycardia. In contrast, parasympathetic activation results in bradycardia, vasodilation, sympathetic inhibition, and inhibition of vasopressin release.

Neural stimulation can be used to stimulate nerve traffic or inhibit nerve traffic. An example of neural stimulation to stimulate nerve traffic is a lower frequency stimulation signal (e.g. within a range on the order of 20 Hz to 50 Hz). An example of neural stimulation to inhibit nerve traffic is a higher frequency stimulation signal (e.g. within a range on the order of 120 Hz to 150 Hz). Other methods for stimulating and inhibiting nerve traffic have been proposed, including modal block of nerve traffic.

High-amplitude vagal (parasympathetic) stimulation appears to be atrially proarrhythmic; and both sympathetic stimulation and low-amplitude vagal stimulation appear to be atrially anti-arrhythmic. Sympathetic stimulation or parasympathetic inhibition alters the electrophysiologic properties of the atria, prolonging the atrial refractory period and decreasing the rate of atrial tachyarrhythmias. The present subject matter provides a therapy for atrial arrhythmias that uses sympathetic stimulation and/or parasympathetic inhibition to suppress or convert supraventricular arrhythmias. The anti-arrhythmic mechanism may be due to one or more of an increase in atrial refractory period, a reduction in anisotropy, or a reduction of ectopic beats.

Various embodiments detect a supraventricular arrhythmia, such as atrial fibrillation and atrial flutter, and deliver neural stimulation in response to the detected supraventricular arrhythmia to elicit a sympathetic response. The sympathetic response can be elicited by stimulating a sympathetic nerve target, inhibiting a parasympathetic nerve target, or both stimulating a sympathetic nerve target and inhibiting a parasympathetic nerve target. According to various embodiments, a neural stimulator uses a neural stimulation element such as nerve cuff electrodes and intravascularly-fed electrodes to transvascularly stimulate a neural target. According to various embodiments, the neural stimulation element includes a transducer adapted to deliver ultrasound energy, a transducer adapted to deliver light energy, a transducer adapted to deliver magnetic energy, or a transducer adapted to deliver thermal energy.

In order to elicit a sympathetic response by stimulation of a sympathetic nerve target, some embodiments stimulate sympathetic ganglion, and some embodiments stimulate a cardiac sympathetic nerve. In order to elicit a sympathetic response by inhibiting parasympathetic nerve traffic, some embodiments inhibit parasympathetic traffic in the vagus nerve or a branch thereof. Some embodiments inhibit vagal nerve activity by applying a low amplitude parasympathetic stimulation of the vagus nerve. Other ways for inhibiting parasympathetic nerve traffic can be used, such as inhibiting neural activity in parasympathetic neural targets such as baroreceptors and cardiac fat pads.

According to various embodiments, the supraventricular arrhythmia is detected using electrodes such as subcutaneous electrodes integrated into the pulse generator or electrodes on one or more intracardiac leads. The atrial arrhythmia may be able to be detected using an atrial electrogram, or with existing cardiac rhythm management (CRM) supraventricular discrimination algorithms. For example, implantable cardiac defibrillators can apply a supraventricular tachycardia discrimination algorithm to determine whether ventricular activity originates in the ventricles and can be treated with a ventricular shock or if the ventricular activity is caused by a supraventricular tachycardia. However, in the present subject matter, the supraventricular tachycardia is detected before the therapy for the supraventricular tachycardia is delivered. Morphology and stability can be used to determine if a supraventricular tachycardia is present. The QRS waveform pattern for a ventricular tachycardia is different from the QRS waveform pattern for a supraventricular tachycardia is different. The ORS wave is narrower for the supraventricular tachycardia. Stability refers to the rate stability of the tachyarrhythmia. Steadier ventricular rates typically indicate a supraventricular arrhythmia, and more irregular ventricular rates typically indicate a ventricular tachyarrhythmia. A sensing electrode in the atria can be used to provide an atrial electrogram for detecting an atrial tachyarrhythmia. A sensing lead in the ventricle can be used, in conjunction with discrimination algorithms, to determine if the ventricular activity is attributable to a supraventricular tachyarrhythmia. ECG electrodes, such as may be placed on the can of the implantable device, can be used in conjunction with discrimination algorithms to identify QRS waveforms attributable to a supraventricular tachyarrhythmia.

Various embodiments provide neural stimulation therapy for atrial arrhythmias in conjunction with one or more other atrial therapies, such as anti-tachycardia pacing, low-energy cardioversion, anti-arrhythmia shocks, and drug delivery. The neural stimulation therapy and any of these other therapies may be applied simultaneously, in a synchronized fashion, or in a tiered fashion.

As a prolonged sympathetic response is undesirable, temporary neural stimulation to elicit the sympathetic response is provided in response to a detected supraventricular arrhythmia, or a detected supraventricular precursor to a supraventricular arrhythmia. For example, the neural stimulation may be temporarily delivered for a duration of seconds to minutes. An embodiment, for example, provides the neural stimulation in response to a detected supraventricular arrhythmia for a duration within a range between ten seconds to two minutes. The duration is not necessarily limited to the ten second to two minute range.

Some embodiments place a lead in a vessel near the stellate ganglion to transvascularly stimulate the stellate ganglion. Some embodiments place a cuff or proximate lead to the stellate ganglion for use in stimulating the stellate ganglion. Some embodiments place a lead on or near the cervical sympathetic trunk; and some embodiments place a lead on or near the cervical vagus nerve. Some embodiments access both the cervical sympathetic trunk and the cervical vagus nerve to permit both sympathetic stimulation and to also permit parasympathetic sensing and/or stimulation. Some embodiments use a combination or bifurcated lead to access both the cervical sympathetic trunk and the cervical vagus nerve.

FIG. 1 illustrates an embodiment of an atrial arrhythmia therapy. In the illustrated embodiment, a supraventricular arrhythmia is detected at 101. The supraventricular arrhythmia may be an atrial flutter or an atrial fibrillation, for example. At 101, various embodiments search for and detect a specific supraventricular arrhythmia that is amenable to neural stimulation treatment that elicits a sympathetic response. A precursor for a supraventricular arrhythmia may be detected at 101, and a prophylactic therapy may be applied in response. The supraventricular can be detected using an atrial electrogram or using various known discrimination algorithms. If a supraventricular arrhythmia is detected, the process proceeds to 102, where neural stimulation is delivered to elicit a sympathetic response, through stimulation of a sympathetic neural target and/or inhibition of a parasympathetic neural target. The neural stimulation is delivered to suppress or convert supraventricular arrhythmias.

The process illustrated in FIG. 1 illustrates a detected supraventricular arrhythmia. The decision at 101 can be whether a supraventricular arrhythmia event has occurred, where a supraventricular arrhythmia event may include a precursor of a supraventricular arrhythmia episode or the supraventricular arrhythmia episode itself. The neural stimulation to elicit a sympathetic response, illustrated at 102, is a supraventricular arrhythmia treatment, which may include a prophylactic treatment for supraventricular arrhythmia in response to a detected precursor, or a therapeutic treatment for a detected episode of supraventricular arrhythmia.

Figure 2:
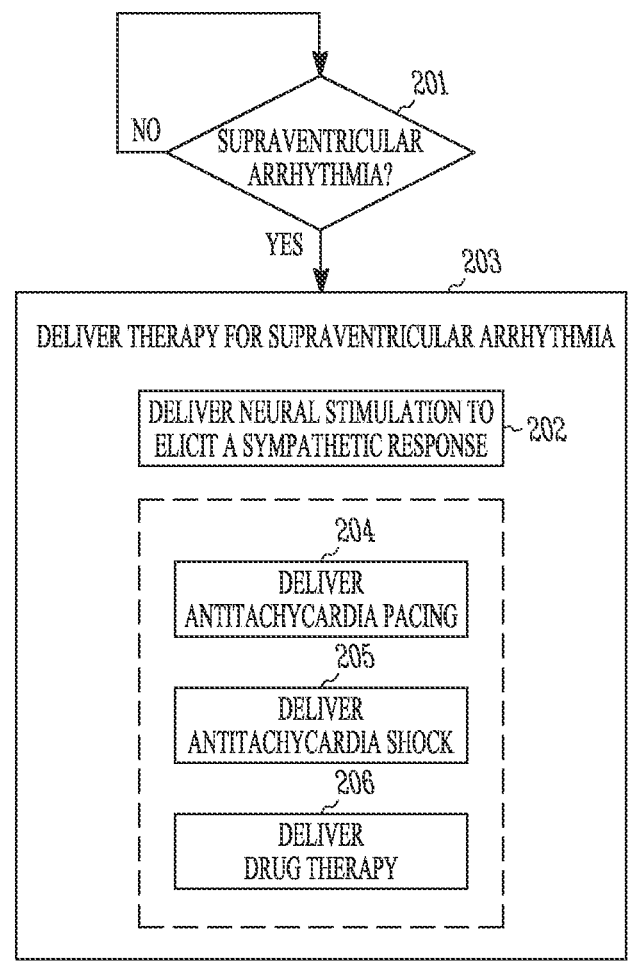
FIG. 2 illustrates neural stimulation therapy for atrial arrhythmias in conjunction with one or more other atrial therapies, according to various embodiments.

FIG. 2 illustrates neural stimulation therapy for atrial arrhythmias in conjunction with one or more other atrial therapies, according to various embodiments. At 201, it is determined whether there is a supraventricular arrhythmia for which a therapy wilt be delivered. If such a supraventricular arrhythmia is detected, the process proceeds to 203 to deliver a therapy for the detected supraventricular arrhythmia. The therapy delivered at 203 includes delivering neural stimulation to elicit a sympathetic response, as illustrated at 202. According to various embodiments, the therapy delivered at 203 also includes delivering antitachycardia pacing at 204. According to various embodiments, the therapy delivered at 203 also includes delivering an antitachycardia shock at 205. According to various embodiments, the therapy delivered at 203 also includes delivering antiarrhythmia drug therapy at 206. Some embodiments include various combinations of two or more of these other therapies 204, 205, and/or 206. Any of these other therapies 204, 205, and/or 206 may be applied simultaneously, in a synchronized fashion, or in a tiered fashion with the neural stimulation.

By way of example and not limitation, various embodiments respond to a detected supraventricular arrhythmia by delivering neural stimulation. If the neural stimulation does not suppress or convert the supraventricular arrhythmia, an antitachycardia pacing (ATP) is delivered, followed by an antitachycardia shock if the ATP is not successful in suppressing or converting the supraventricular arrhythmia. Some embodiments terminate the neural stimulation before delivering the ATP, and some embodiments deliver the neural stimulation simultaneously with the neural stimulation. In embodiments that deliver the neural stimulation simultaneously with the neural stimulation, some embodiments deliver the neural stimulation first, and then add ATP therapy in addition to the neural stimulation, and some embodiments initially provide the combination of neural stimulation and ATP in response to the detected supraventricular arrhythmia. The particular scheme used for treating the arrhythmia can be preset or can be programmed by a physician.

Figure 3:
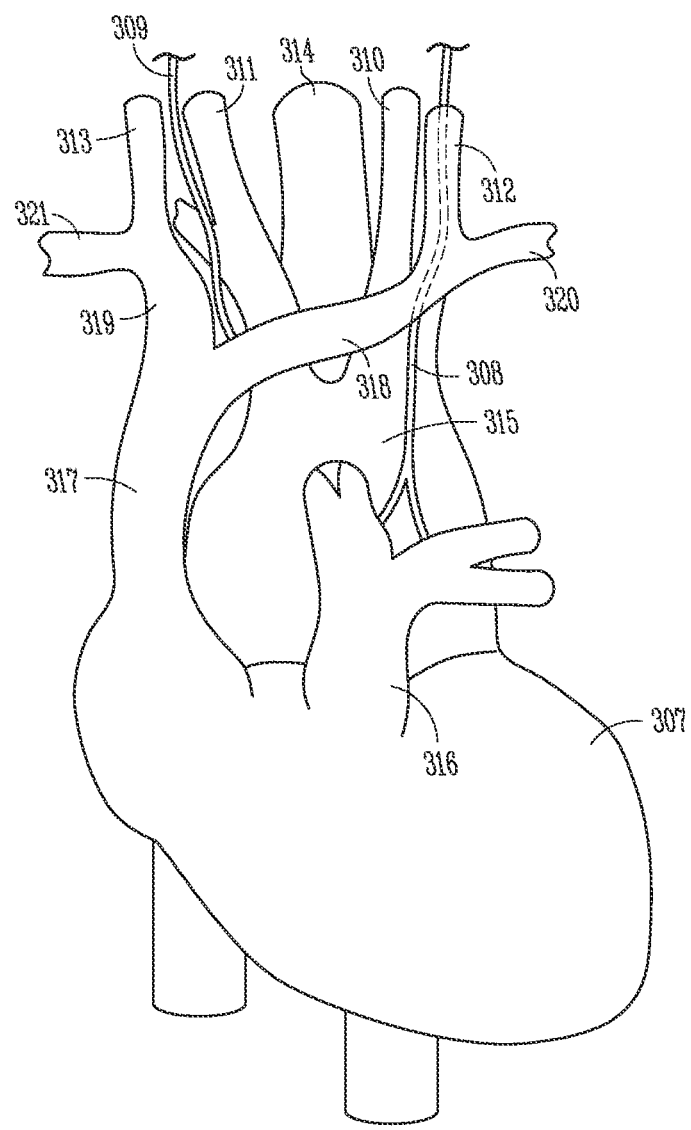
FIG. 3 illustrates a heart and anatomical features in a cervical region, including the left and right vagus nerves, the left and right carotid arteries, and the left and right internal jugular veins.

FIG. 3 illustrates a heart 307 and anatomical features in a cervical region, including the left and right vagus nerves 308 and 309, the left and right carotid arteries 310 and 311, and the left and right internal jugular veins 312 and 313. Also illustrated in FIG. 3 are the trachea 314, pulmonary artery 315, aorta 316, superior vena cava 317, the left and right innominate veins 318 and 319 (also referred to as brachiocephalic veins), and the left and right subclavian veins 320 and 321. Some embodiments transvascularly stimulate a desired neural target. Those of ordinary skill in the art, upon reading and comprehending this disclosure, would understand how to transvascularly stimulate the neural target using vessels such as the innominate, subclavian and internal jugular veins to access the neural target.

Figure 4:
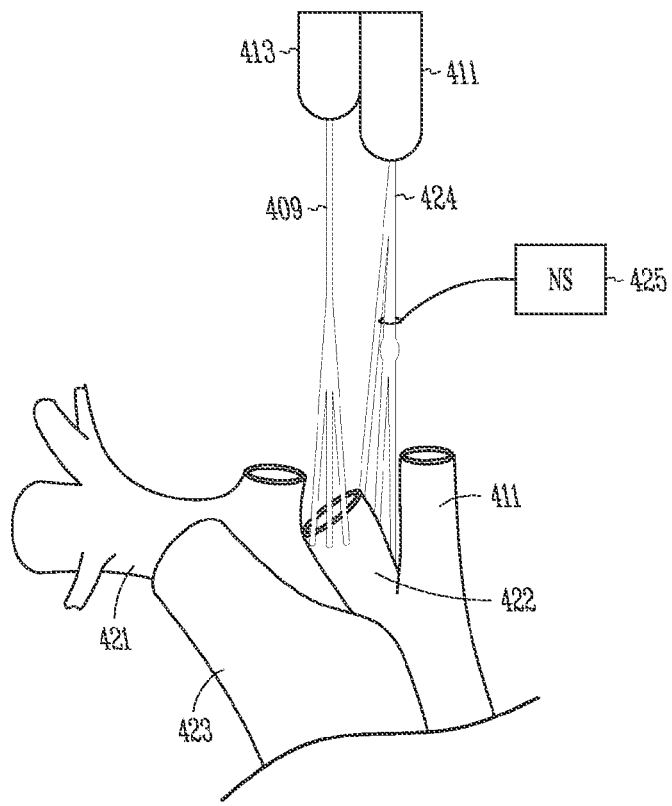
FIG. 4 illustrates an embodiment of a neural stimulator that stimulates sympathetic activity in a cardiac sympathetic nerve.

FIG. 4 illustrates an embodiment of a neural stimulator that stimulates sympathetic activity in a cardiac sympathetic nerve. FIG. 4 illustrates portions of a common carotid artery 411, the internal jugular vein 413, the subclavian vein 421 and the vagus nerve 409. The figure also illustrates portions of the subclavian artery 422, the clavicle 423 and the sympathetic nerve trunk 424. In the embodiment illustrated in FIG. 4, an implantable neural stimulator 425 includes a stimulation lead with a nerve cuff electrode positioned to stimulate the cardiac sympathetic nerve trunk 424 as part of the therapy for a supraventricular arrhythmia.

Figure 5:
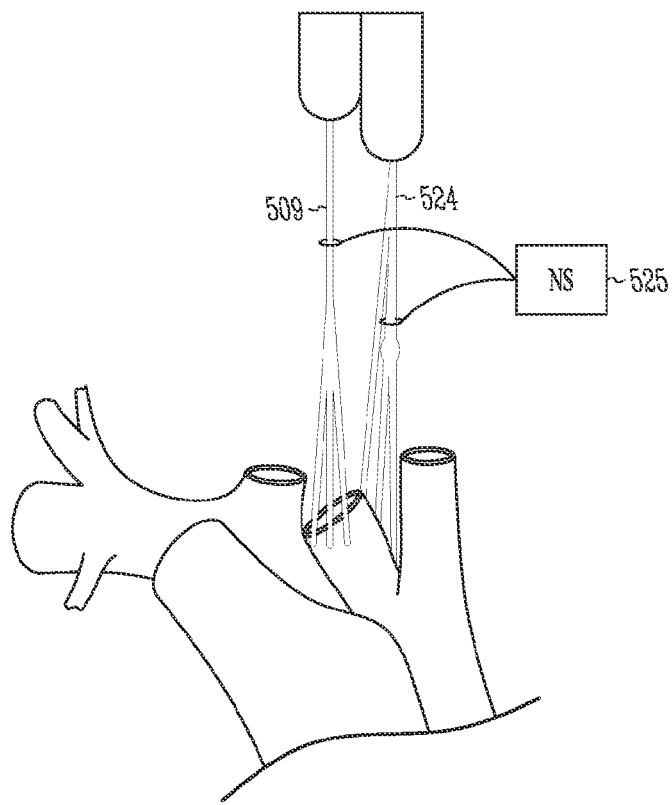
FIG. 5 illustrates a neural stimulator with a lead extending to the cardiac sympathetic nerve and to the vagus nerve.

FIG. 5 illustrates a neural stimulator 525 with a lead extending to the cardiac sympathetic nerve 524 and to the vagus nerve 509. A sympathetic response can be elicited by inhibiting nerve traffic on the vagus nerve and/or stimulating nerve traffic on the cardiac sympathetic nerve. Various embodiments use a sensor to detect nerve traffic at one of the neural locations to control stimulation at the other neural location. For example, one embodiment stimulates the cardiac sympathetic nerve to provide the sympathetic response, and uses vagus nerve activity as feedback to control the neural stimulation of the cardiac sympathetic nerve. Other neural locations can be used in addition to or in place of one or both of the neural locations illustrated in FIG. 5. Also, separate leads can be used, or a bifurcated lead can be used to access the neural locations.

Figure 6:
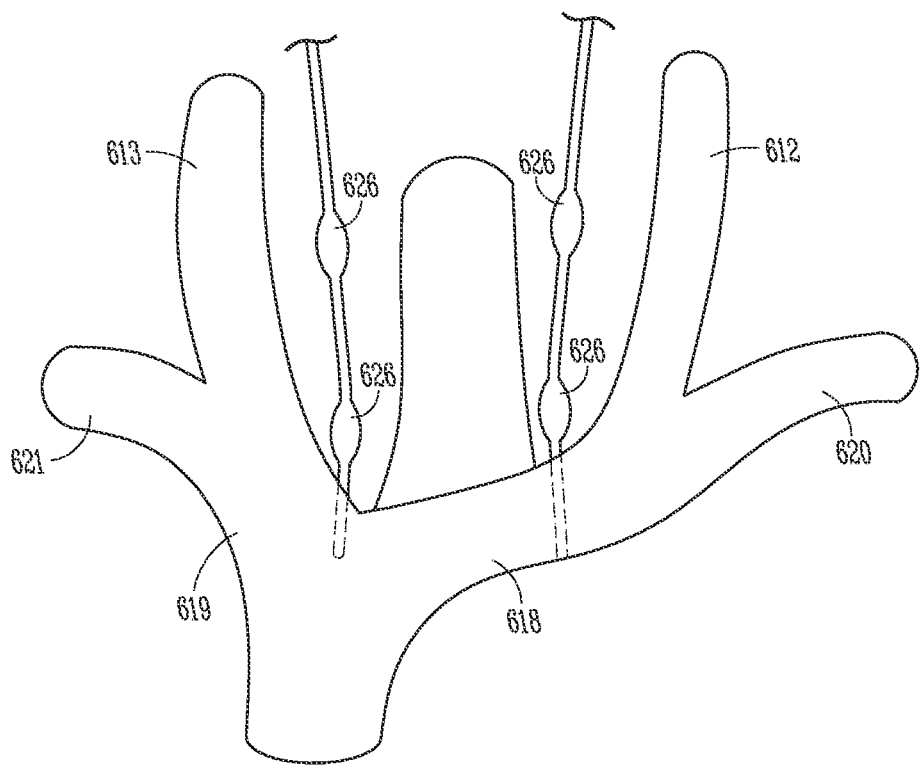
FIG. 6 illustrates sympathetic ganglion proximate to the brachiocephalic or innominate veins, the internal jugular veins and subclavian veins.

FIG. 6 illustrates sympathetic ganglion 626 proximate to the brachiocephalic or innominate veins 618 and 619, the internal jugular veins 612 and 613 and the subclavian veins 620 and 621. The left and right brachiocephalic veins are formed by the union of each corresponding internal jugular vein and subclavian vein. Sympathetic ganglion are formed along the sympathetic nerve trunk. Those of ordinary skill in the art, upon reading and comprehending this disclosure, would understand how to transvascularly stimulate a neural target using vessels such as the innominate, subclavian and internal jugular veins to access the neural target. Those of ordinary skill in the art would also be able to account for anatomical variations in the respective positions of the veins and neural targets. For example, the stellate ganglion, illustrated as the lower two ganglion 626 in the figure, can be transvascularly stimulated through a vein such as the subclavian or innominate veins. The vagus nerve, such as illustrated in FIG. 5, can also be transvascularly stimulated from the internal jugular vein. In a bifurcated lead embodiment, by way of example and not limitation, one branch of the lead is fed into the internal jugular vein to access a vagus nerve, and the other branch of the lead is fed into the subclavian vein. If the stellate ganglion is capable of being stimulated from the innominate vein, a single, combination lead can be fed through the innominate vein for use in stimulating the stellate ganglion, and then further fed into the internal jugular vein for use in stimulating the vagus nerve and/or sensing neural traffic on the vagus nerve.

Figure 7:
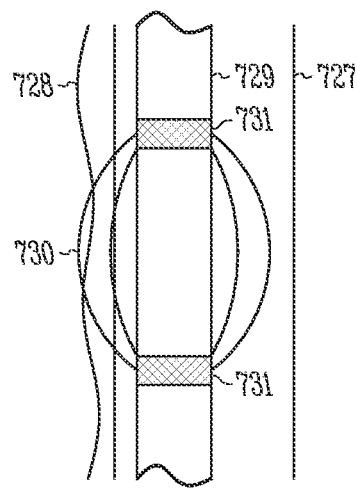
FIG. 7 illustrates a transluminal neural stimulation using electrodes within the lumen, according to various embodiments.

FIG. 7 illustrates a transluminal neural stimulation using electrodes within a lumen or vasculature, according to various embodiments. The figure illustrates a lumen 727 (e.g. subclavian, internal jugular, or innominate veins), a nerve 728 or ganglion external to the lumen, and a lead 729 within the lumen. The neural stimulation generates an electrical field 730 between electrodes 731. The electric field extends past the lumen wall to the nerve.

Figure 8:
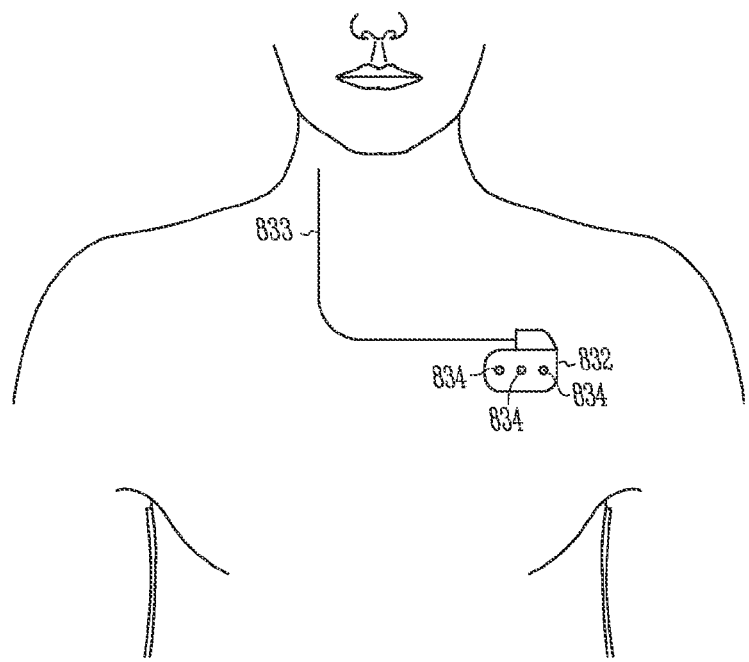
FIG. 8 illustrates a system embodiment in which an IMD is placed subcutaneously or submuscularly in a patient's chest with lead(s) positioned to stimulate a vagus nerve.

FIG. 8 illustrates a system embodiment in which an implantable medical device (IMD) 832 is placed subcutaneously or submuscularly in a patient's chest with lead(s) 833 positioned to stimulate a neural target in the cervical region (e.g. a vagus nerve or cardiac sympathetic nerve). According to various embodiments, neural stimulation lead(s) 833 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein, and stimulate the stellate ganglion using electrode(s) positioned within the subclavian and/or innominate veins. The neural targets can be stimulated using other energy waveforms, such as ultrasound and light energy waveforms. Other neural targets can be stimulated, such as cardiac nerves and cardiac fat pads. The illustrated system includes leadless ECU electrodes on the housing of the device. These ECG electrodes 834 are capable of being used to detect heart rate, for example.

Figure 9:
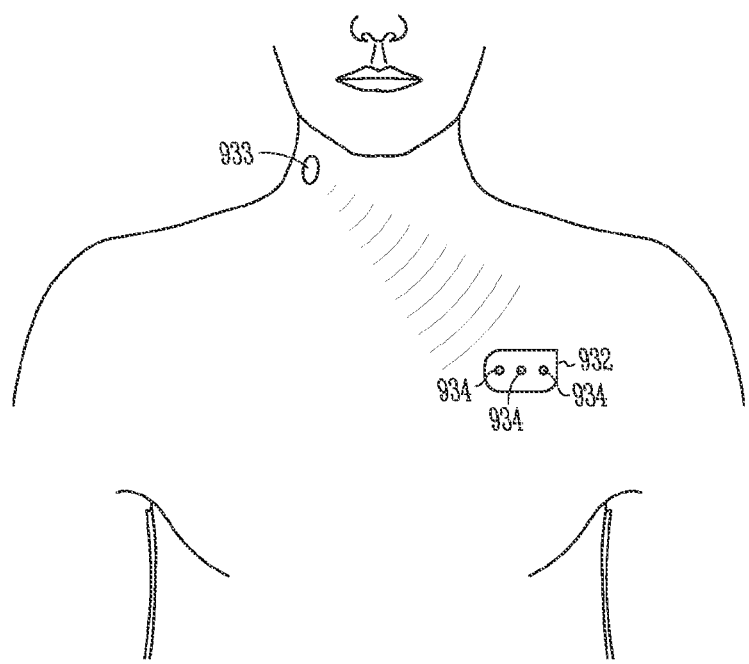
FIG. 9 illustrates a system embodiment that includes an implantable medical device (IMD) with satellite electrode(s) positioned to stimulate at least one neural target.

FIG. 9 illustrates a system embodiment that includes an implantable medical device (IMD) 932 with satellite electrode(s) 933 positioned to stimulate at least one cervical neural target (e.g. vagus nerve, cardiac sympathetic nerve, and stellate ganglion). The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. Various embodiments include satellite neural stimulation transducers used to generate neural stimulation waveforms such as ultrasound and light waveforms. The illustrated system includes leadless ECG electrodes on the housing of the device. These ECG electrodes 934 are capable of being used to detect heart rate, for example.

Figure 10:
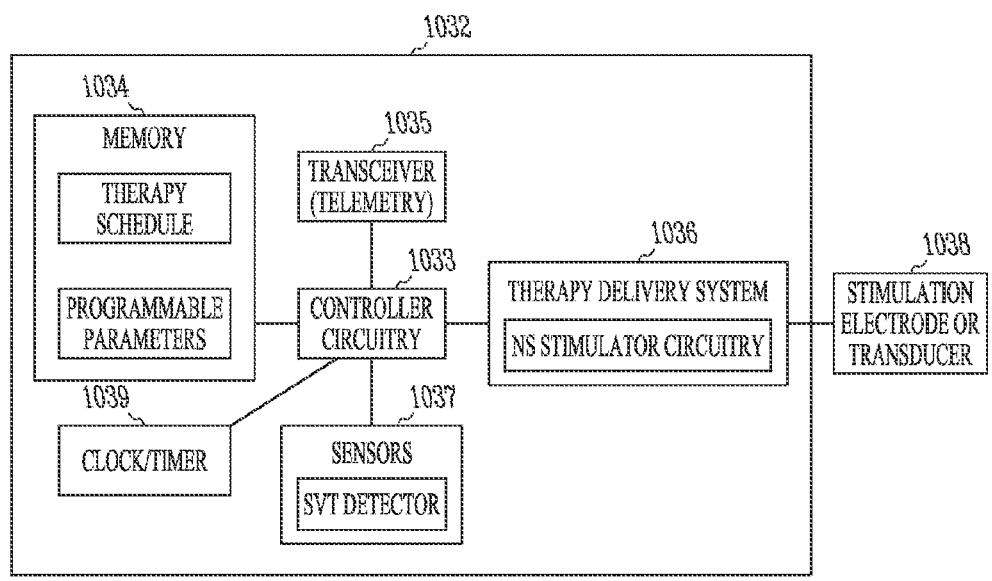
FIG. 10 illustrates an implantable medical device (IMD), according to various embodiments of the present subject matter.

FIG. 10 illustrates an implantable medical device (IMD) 1032, according to various embodiments of the present subject matter. The illustrated IMD 1032 provides neural stimulation signals for delivery to predetermined neural targets to provide supraventricular arrhythmia therapy using an elicited neural stimulation response. The illustrated device includes controller circuitry 1033 and memory 1034. The controller circuitry is capable of being implemented using hardware, software, and combinations of hardware and software. For example, according to various embodiments, the controller circuitry includes a processor to perform instructions embedded in the memory to perform functions associated with the neural stimulation therapy. The illustrated device further includes a transceiver 1035 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device further includes a therapy delivery system 1036, such as neural stimulation circuitry. Other therapy delivery systems, such as drug delivery systems, can be also used. The illustrated device also includes sensor circuitry 1037. The sensor circuitry can be used to detect a supraventricular arrhythmia to trigger the therapy delivery.

Some embodiments uses sensor circuitry adapted to detect nerve traffic for use in providing neural stimulation control feedback. Other physiological parameters, such as heart rate, respiration, and blood pressure can be sensed to provide neural stimulation control feedback. According to some embodiments, one or more leads are able to be connected to the sensor circuitry and neural stimulation circuitry. Some embodiments use wireless connections between the sensor(s) and sensor circuitry, and some embodiments use wireless connections between the stimulator circuitry and electrodes. According to various embodiments, the neural stimulation circuitry is used to apply electrical stimulation pulses to desired neural targets, such as through one or more stimulation electrodes 1038 positioned at predetermined location(s). Some embodiments use transducers to provide other types of energy, such as ultrasound, light or magnetic energy. The controller circuitry can control the therapy provided by system using a therapy schedule in memory 1034, or can compare a target range (or ranges) of the sensed physiological response(s) stored in the memory 1034 to the sensed physiological response(s) to appropriately adjust the intensity of the neural stimulation/inhibition, The target range(s) can be programmable.

According to various embodiments using neural stimulation, the stimulation circuitry 1036 is adapted to set or adjust any one or any combination of stimulation features. Examples of stimulation features include the amplitude, frequency, polarity and wave morphology of the stimulation signal. Examples of wave morphology include a square wave, triangle wave, sinusoidal wave, and waves with desired harmonic components to mimic white noise such as is indicative of naturally-occurring baroreflex stimulation. Some embodiments of the neural stimulation circuitry are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry are adapted to generate a stimulation signal with a predetermined frequency, and are further adapted to respond to a control signal from the controller to modify the frequency of the stimulation signal.

The controller 1033 can be programmed to control the neural stimulation delivered by the stimulation circuitry 1036 according to stimulation instructions, such as a stimulation schedule, stored in the memory 1034. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time.

According to some embodiments, the controller 1033 controls the neural stimulation generated by the stimulation circuitry by initiating each pulse of the stimulation signal. In some embodiments, the controller circuitry initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the controller 1033 controls the stimulation circuitry 1036 to initiate a neural stimulation session and to terminate the neural stimulation session. The burst duration of the neural stimulation session under the control of the controller 1033 can be programmable. The controller may also terminate a neural stimulation session in response to an interrupt signal, such as may be generated by one or more sensed parameters or any other condition where it is determined to be desirable to stop neural stimulation.

The illustrated device includes a clock or timer 1039 which can be used to execute the programmable stimulation schedule. For example, a physician can program a daily schedule of therapy based on the time of day if the detected supraventricular arrhythmia if the severity of the arrhythmia is such that therapy can wait until a more convenient time for the patient. A stimulation session can begin at a first programmed time, and can end at a second programmed time. Various embodiments initiate and/or terminate a stimulation session based on a signal triggered by a user. Various embodiments use sensed data to enable and/or disable a stimulation session. Thus, for example, the dock can be used to provide an enabling condition for the therapy in addition to a detected supraventricular arrhythmia event By way of another example of a two or more conditions functioning together to enable a therapy, an activity sensor and the supraventricular arrhythmia detector can function together to provide supraventricular arrhythmia treatment only during periods of lower activity, as determined by a detected activity below an activity threshold.

According to various embodiments, the schedule refers to the time intervals or period when the neural stimulation therapy is delivered. A schedule can be defined by a start time and an end time, or a start time and a duration. Various device embodiments apply the therapy according to the programmed schedule contingent on enabling conditions in addition to a detected supraventricular arrhythmia, such as patient rest or sleep, tow heart rate levels, time of day, and the like. The therapy schedule can also specify how the stimulation is delivered, such as continuously at the pulse frequency throughout the identified therapy period (e.g. 5 Hz pulse frequency for two minutes), or according to a defined duty cycle during the therapy delivery period (e.g. 10 seconds per minute at 5 Hz pulse frequency for two minutes). As illustrated by these examples, the therapy schedule is distinguishable from the duty cycle.

Figure 11:
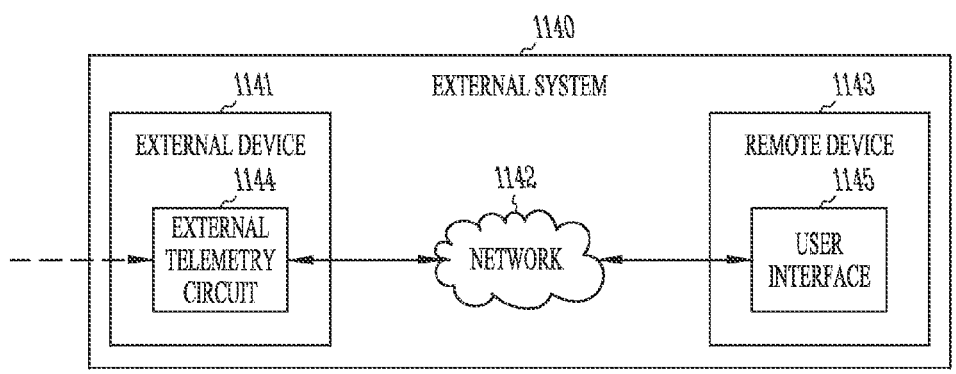
FIG. 11 is a block diagram illustrating an embodiment of an external system.

FIG. 11 is a block diagram illustrating an embodiment of an external system 1140. The external system includes a programmer, in some embodiments. In the illustrated embodiment, the external system includes a patient management system. As illustrated, the external system 1140 is a patient management system including an external device 1141, a telecommunication network 1142, and a remote device 1143. External device 1141 is placed within the vicinity of an implantable medical device (IMD) and includes external telemetry system 1144 to communicate with the IMD. Remote device(s) 1143 is in one or more remote locations and communicates with external device 1141 through network 1142, thus allowing a physician or other caregiver to monitor and treat a patient from a distant location and/or allowing access to various treatment resources from the one or more remote locations. The illustrated remote device 1143 includes a user interface 1145. According to various embodiments, the external device includes a programmer or other device such as a computer, a personal data assistant or phone. The external device 1141, in various embodiments, includes two devices adapted to communicate with each other over an appropriate communication channel, such as a computer and a Bluetooth enabled portable device (e.g. personal digital assistant, phone), by way of example and not limitation.

Figure 12:
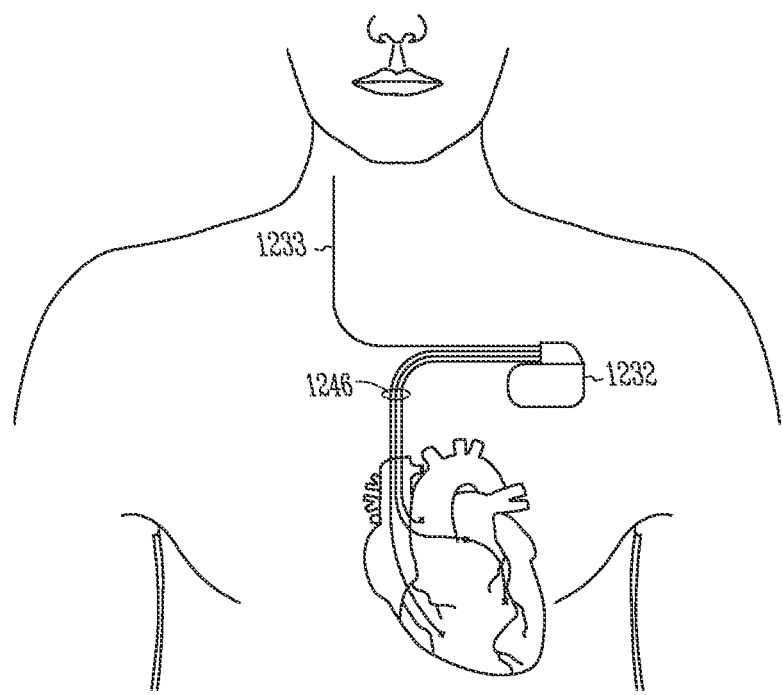
FIG. 12 illustrates an IMD placed subcutaneously or submuscularly in a patient's chest with lead(s) positioned to provide a CRM therapy to a heart, and with lead(s) positioned to stimulate and/or inhibit neural traffic at a cervical neural target, according to various embodiments.

FIG. 12 illustrates an IMD 123 placed subcutaneously or submuscularly a patient's chest with lead(s) 1246 positioned to provide a CRM therapy to a heart, and with lead(s) 1233 positioned to stimulate and/or inhibit neural traffic at a cervical neural target, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein and some embodiments stimulate the stellate ganglion using electrode(s) positioned within the subclavian and/or innominate veins.

Figure 13:
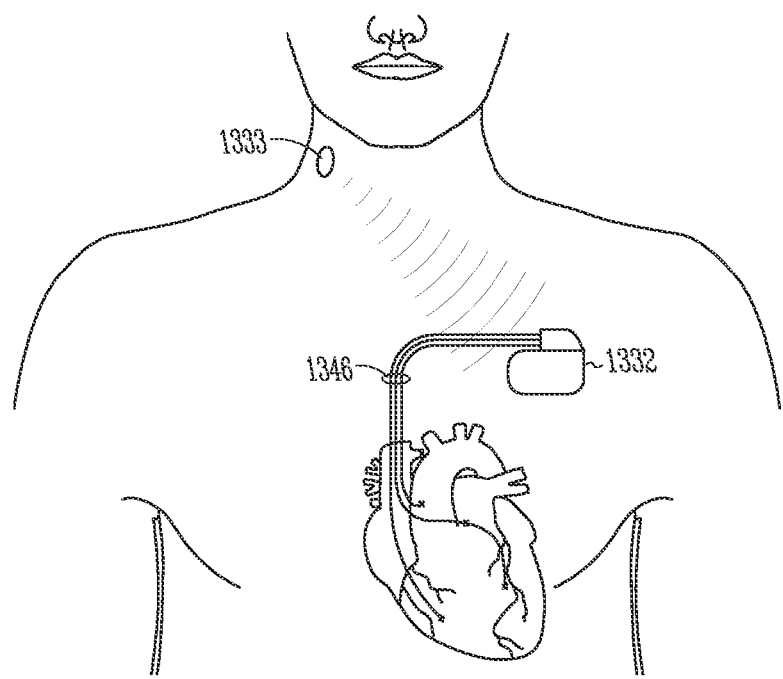
FIG. 13 illustrates an IMD with lead(s) positioned to provide a CRM therapy to a heart, and with satellite transducers positioned to stimulate/inhibit a cervical neural target, according to various embodiments.

FIG. 13 illustrates an IMD 1332 with lead(s) 1346 positioned to provide a CRM therapy to ahead, and with satellite transducers 1333 positioned to stimulate/inhibit a cervical neural target, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous electrodes, nerve cuff electrodes and intravascular electrodes.

Figure 14:
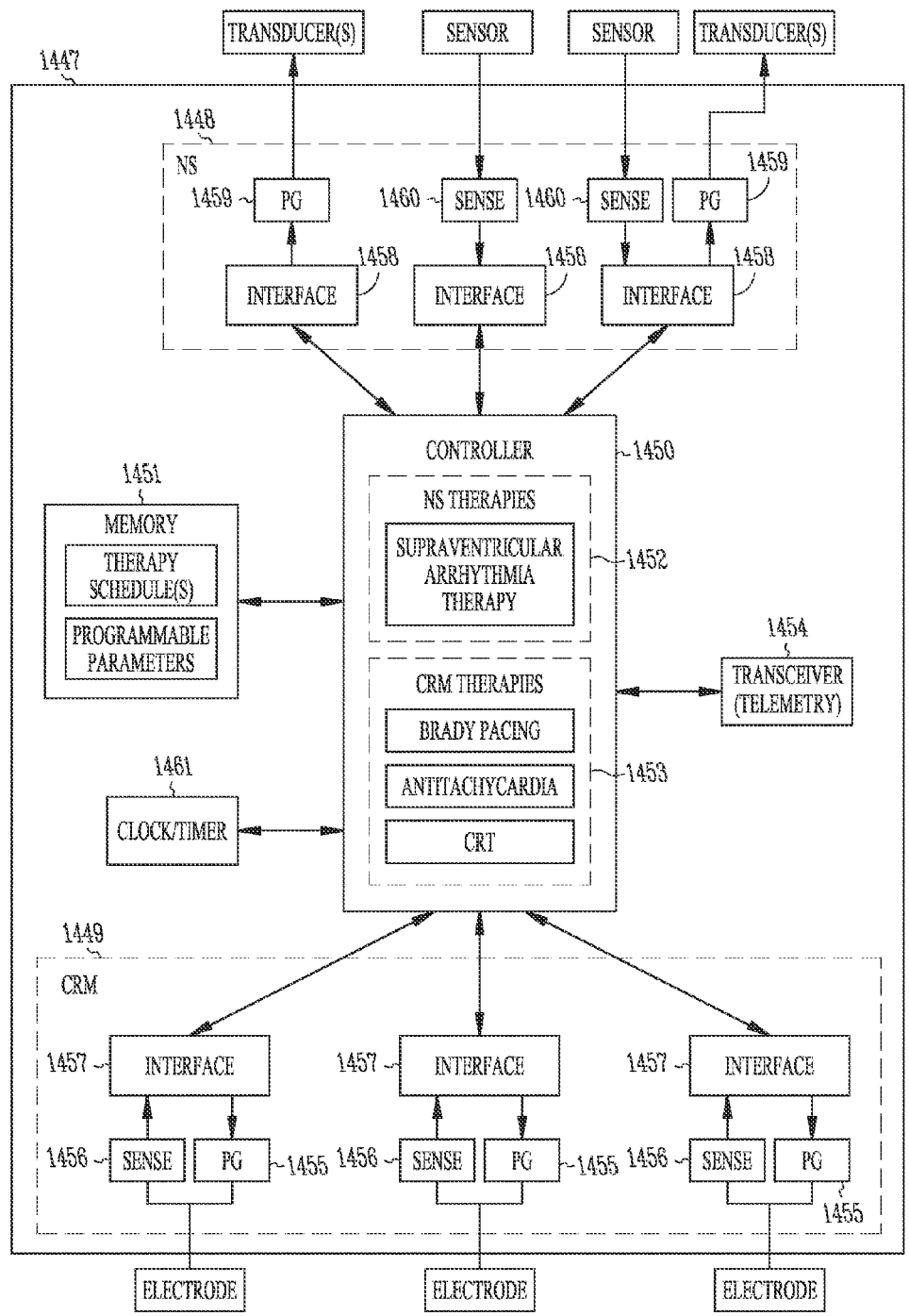
FIG. 14 illustrates an implantable medical device (IMD) having a neural stimulation (NS) component and a cardiac rhythm management (CRM) component according to various embodiments of the present subject matter.

FIG. 14 illustrates an implantable medical device (IMD) 1447 having a neural stimulation (NS) component 1448 and a cardiac rhythm management (CRM) component 1449 according to various embodiments of the present subject matter. The illustrated device includes a controller 1450 and memory 1451. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. For example, therapy schedule(s) and programmable parameters can be stored in memory. According to various embodiments, the controller includes a processor to execute instructions embedded in memory to perform the neural stimulation and CRM functions. The illustrated neural stimulation therapy 1452 includes an supraventricular arrhythmia therapy. Various embodiments include CRM therapies 1453, such as bradycardia pacing, anti-tachycardia therapies such as ATP, defibrillation and cardioversion, and cardiac resynchronization therapy (CRT). The illustrated device further includes a transceiver 1454 and associated circuitry for use to communicate with a programmer or another external or internal device. Various embodiments include a telemetry coil.

The CRM therapy section 1449 includes components, under the control of the controller, to stimulate a heart and/or sense cardiac signals using one or more electrodes. The illustrated CRM therapy section includes a pulse generator 1455 for use to provide an electrical signal through an electrode to stimulate a heart, and further includes sense circuitry 1456 to detect and process sensed cardiac signals. An interface 1457 is generally illustrated for use to communicate between the controller 1450 and the pulse generator 1455 and sense circuitry 1456. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 1448 includes components, under the control of the controller, to stimulate a neural stimulation target and/or sense parameters associated with nerve activity or surrogates of nerve activity such as heart rate, blood pressure and respiration. Three interfaces 1458 are illustrated for use to provide neural stimulation. However, the present subject matter is not limited to a particular number interfaces, or to any particular stimulating or sensing functions. Pulse generators 1459 are used to provide electrical pulses to transducer or transducers for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 1460 are used to detect and process signals from a sensor, such as a sensor of nerve activity, heart rate, blood pressure, respiration, and the like. The interfaces 1158 are generally illustrated for use to communicate between the controller 1450 and the pulse generator 1459 and sense circuitry 1460. Each interface, for example, may be used to control a separate lead. Various embodiments of the NS therapy section only includes a pulse generator to stimulate a neural target. The illustrated device further includes a clock/timer 1461, which can be used to deliver the programmed therapy according to a programmed stimulation protocol and/or schedule.

Figure 15:
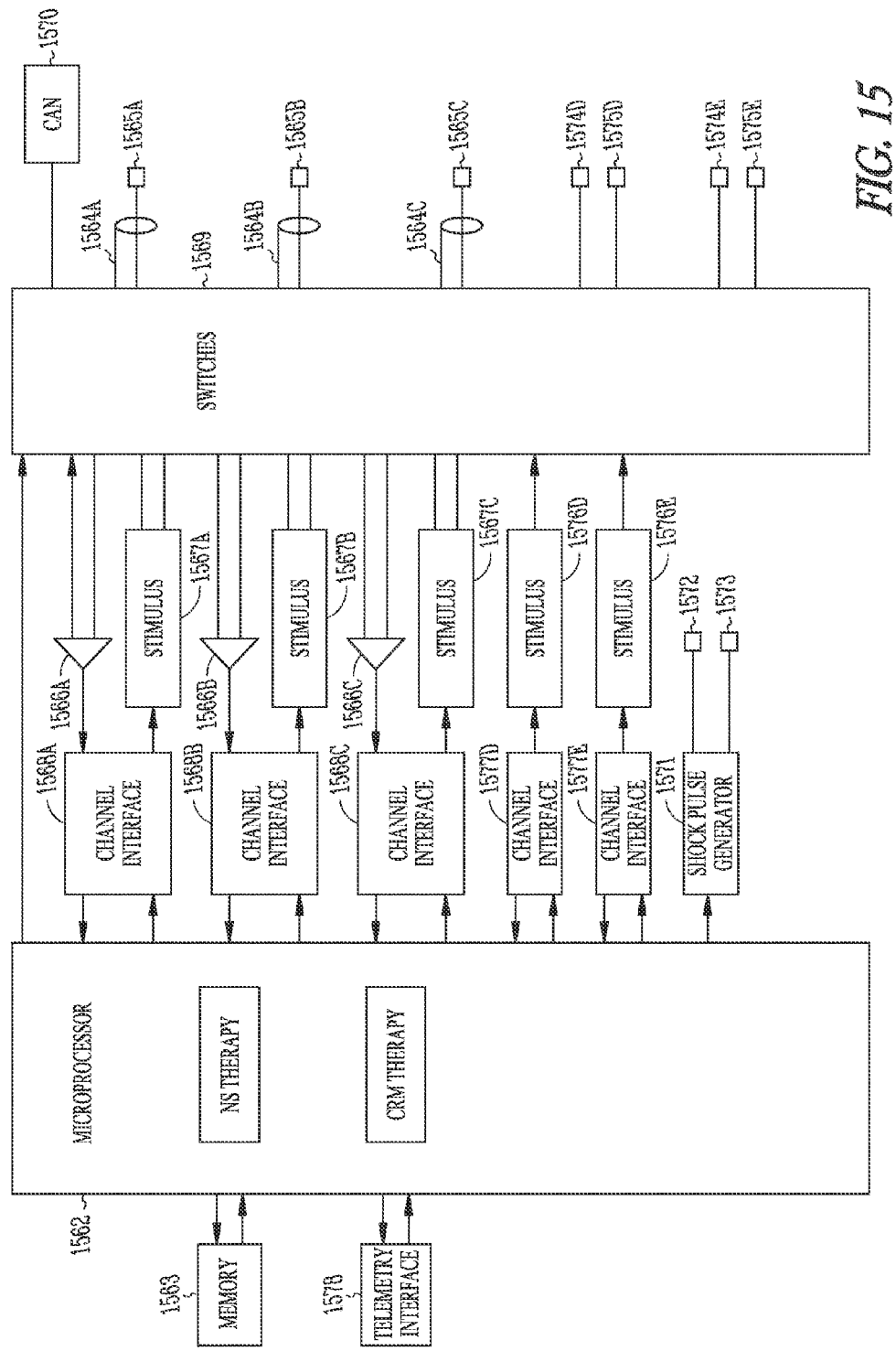
FIG. 15 shows a system diagram of an embodiment of a microprocessor-based implantable device, according to various embodiments.

FIG. 15 shows a system diagram of an embodiment of a microprocessor-based implantable device, according to various embodiments. The controller of the device is a microprocessor 1562 which communicates with a memory 1563 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1564A-C and tip electrodes 1565A-C, sensing amplifiers 1566A-C, pulse generators 1567A-C, and channel interfaces 1568A-C, Each channel thus includes a pacing channel made up of the pulse generator connected to the electrode and a sensing channel made up of the sense amplifier connected to the electrode. The channel interfaces 1568A-C communicate bidirectionally with the microprocessor 1562, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 1569 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1570 or an electrode on another lead serving as a ground electrode. A shock pulse generator 1571 is also interfaced to the controller for delivering a defibrillation shock via a pair of shock electrodes 1572 and 1573 upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 1574D and a second electrode 1575D, a pulse generator 1576D, and a channel interface 1577D, and the other channel includes a bipolar lead with a first electrode 1574E and a second electrode 1575E, a pulse generator 1576E, and a channel interface 1577E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 1578 connected to the microprocessor, which can be used to communicate with an external device. The illustrated microprocessor 1562 is capable of performing neural stimulation therapy routines and myocardial (CRM) stimulation routines. Examples of NS therapy routines include a supraventricular arrhythmia therapy that uses neural stimulation that elicits a sympathetic response. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

According to various embodiments, the device, as illustrated and described above, is adapted to deliver neural stimulation as electrical stimulation to desired neural targets, such as through one or more stimulation electrodes positioned at predetermined location(s). Other elements for delivering neural stimulation can be used. For example, some embodiments use transducers to deliver neural stimulation using other types of energy, such as ultrasound, light, magnetic or thermal energy.

One of ordinary skill in the art will understand that, the modules and other circuitry shown and described herein can be implemented using software, hardware, and combinations of software and hardware. As such, the terms module and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof can be combined. In various embodiments, the methods are implemented using a computer data signal embodied in a carrier wave or propagated signal, that represents a sequence of instructions which, when executed by a processor cause the processor to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method, comprising:
   detecting a supraventricular arrhythmia event; and
   delivering a supraventricular arrhythmia treatment in response to a detected supraventricular arrhythmia event, including delivering closed-loop neural stimulation to elicit a sympathetic response, wherein delivering closed-loop neural stimulation includes stimulating a neural target, sensing a physiological response to stimulation of the neural target using a feedback sensor, and using the sensed physiological response to adjust a stimulation intensity of the stimulation for treating the supraventricular event, wherein sensing the physiological response using the feedback sensor includes sensing respiration using a respiration sensor, or sensing blood pressure using a blood pressure sensor, or sensing nerve traffic using a nerve traffic sensor.

2. The method of claim 1, wherein:
   detecting a supraventricular arrhythmia event includes detecting a precursor for a supraventricular arrhythmia episode; and
   delivering closed loop neural stimulation to elicit a sympathetic response includes delivering prophylactic neural stimulation to avoid the supraventricular arrhythmia event.

3. The method of claim 1, wherein:
   detecting a supraventricular arrhythmia event includes detecting a supraventricular arrhythmia episode; and
   delivering closed loop neural stimulation to elicit a sympathetic response includes delivering therapeutic neural stimulation for the supraventricular arrhythmia event.

4. The method of claim 1, wherein delivering closed loop neural stimulation to elicit a sympathetic response is responsive to the detected supraventricular arrhythmia event and is further responsive to at least one additional enabling condition.

5. The method of claim 4, wherein the at least one additional enabling condition includes a clock signal representative of a time range of a day, and the neural stimulation is enabled within the time range.

6. The method of claim 4, wherein the at least one additional enabling condition includes an activity signal representative of detected activity and the neural stimulation is enabled if the detected activity is below an activity threshold.

7. The method of claim 1, wherein delivering neural stimulation to elicit a sympathetic response includes stimulating sympathetic activity in a neural target.

8. The method of claim 7, wherein stimulating sympathetic activity in a neural target includes stimulating neural activity in a stellate ganglion.

9. The method of claim 8, wherein inhibiting parasympathetic activity in a neural target includes inhibiting activity in a vagus nerve or a branch thereof.

10. The method of claim 8, wherein inhibiting parasympathetic activity in a neural target includes inhibiting neural activity from baroreceptors or cardiac fat pads.

11. The method of claim 7, wherein stimulating sympathetic activity in a neural target includes stimulating neural activity in a cardiac sympathetic nerve.

12. The method of claim 1, wherein delivering closed loop neural stimulation to elicit a sympathetic response includes inhibiting parasympathetic activity in a neural target.

13. The method of claim 1, wherein delivering closed loop neural stimulation to elicit a sympathetic response includes transvascularly stimulating a neural target using an electric stimulation signal delivering through at least one intravascularly-positioned electrode.

14. The method of claim 1, wherein delivering closed loop neural stimulation to elicit a sympathetic response includes stimulating a neural target using an electric stimulation signal delivered through at least one electrode in a nerve cuff.

15. The method of claim 1, wherein delivering a treatment in response to a detected supraventricular arrhythmia event further includes delivering antitachycardia pacing, delivering an antitachycardia shock, or delivering a drug therapy.

16. A method, comprising:
detecting a supraventricular arrhythmia event, and
delivering a closed-loop supraventricular arrhythmia treatment in response to a detected supraventricular arrhythmia event, including:
   delivering neural stimulation to elicit a sympathetic response;
   sensing a physiological response to the delivered neural stimulation using a feedback sensor selected from the group of feedback sensors consisting of:
      a respiration sensor, a blood pressure sensor, and a nerve traffic sensor; and
   adjusting the neural stimulation based on the sensed physiological response.

17. The method of claim 16, wherein:
sensing the physiological response to the neural stimulation includes sensing the physiological response using a physiologic sensor distinct from that detecting the supraventricular arrhythmia event; and
adjusting the neural stimulation delivery scheme includes comparing the sensed physiologic sensor response to a target range for the sensed physiologic response and altering a stimulation schedule, a duration, a duty cycle, or a stimulation intensity of the neural stimulation based on the comparison.

18. The method of claim 17, wherein sensing the physiological response includes sensing a blood pressure response, and adjusting the neural stimulation includes adjusting the neural stimulation based on the sensed blood pressure response.

19. The method of claim 17, wherein sensing the physiological response includes sensing a respiration response to stimulation of the neural target, and adjusting the neural stimulation includes adjusting the neural stimulation based on the sensed respiration response.

20. The method of claim 17, wherein sensing the physiological response includes sensing nerve traffic.

* * * * *